United States Patent [19]

Lin

[11] 4,056,612

[45] Nov. 1, 1977

[54] AIR FRESHENER GELS

[75] Inventor: Chii-Fa Lin, Tarrytown, N.J.

[73] Assignee: Stauffer Chemical Company, Westport, Conn.

[21] Appl. No.: 635,553

[22] Filed: Nov. 26, 1975

Related U.S. Application Data

[63] Continuation of Ser. No. 453,442, March 21, 1974, abandoned.

[51] Int. Cl.$^2$ ............................................. A61L 13/00
[52] U.S. Cl. .................................................... 424/76
[58] Field of Search ......................................... 424/76

[56] References Cited

U.S. PATENT DOCUMENTS 2,927,055   3/1960   Lanzet ..................................... 424/76

FOREIGN PATENT DOCUMENTS 895,825   3/1972   Canada.

*Primary Examiner*—V. D. Turner
*Attorney, Agent, or Firm*—Paul J. Juettner

[57] ABSTRACT

An air freshener gel consisting essentially of a novel gelling agent and an aqueous medium containing a volatile air freshener component. The novel gelling agent comprises carrageenan, locut bean gum, and a water soluble ammonium salt having a pH greater than about 5.0. The carrageenan contains at least 40% by weight of the carrageenan, kappa carrageenan. The improved air freshener gels exhibit practically no syneresis, improved water gel strength, and water viscosity.

16 Claims, No Drawings

AIR FRESHENER GELS

This is a continuation, of application Ser. No. 453,442 filed Mar. 21, 1974, now abandoned.

BACKGROUND OF THE INVENTION

This invention relates to an improved air freshener gel wherein an aqueous medium containing a volatile air freshener component is gelled by a new gelling agent composition. More particularly, the invention relates to a new gelling agent composition comprising carrageenan, locust bean gum, and ammonium chloride, wherein the carrageenan contains at least 40%, by weight of the carrageenan, kappa carrageenan.

Air freshener gels and their gelling agents are well known. Generally, air freshener gels comprise an aqueous medium containing a volatile air freshener component and a gelling agent which gels the largely aqueous medium. Air freshener gels provide an ideal medium for freshening the air and are popular consumer products.

Air freshener gels operate by continuously releasing the air freshener components from the gel by the room temperature evaporation of the aqueous medium within the gel. The volatile air freshener components can include disinfectants, bactericides, insecticides, and odoriferous materials, or oils which provide a pleasant odor and/or reduce unpleasant odors.

Heretofore, in accordance with U.S. Pat. No. 2,927,055, air freshener gels were prepared by employing as a gelling agent a formulation of carrageenan, locust bean gum, and potassium chloride in conjunction with sodium carboxymethylcellulose. In accordance with the patent, the components and proportions of components of the formulation of gelling agent range as follows in percent, by weight of the complete gel formulation: 0.75 to 1.8% carrageenan, 0.2 to 0.75% locust bean gum, 0.1 to 0.75% potassium chloride, and 0.15 to 0.7% sodium carboxymethylcellulose. In accordance with U.S. Pat. No. 2,927,055, the air freshener gel is prepared by blending the components of the gelling agent in the dry state, adding the blended components to cold water, and heating the components to 180°–190° F. with stirring, until the solids are completely dispersed. The aqueous dispersion is then cooled to 170° F. and the preblended air freshener components added with stirring until a uniform dispersion results, tranferring the dispersion to a molding means, and cooling to produce the formed gel.

In accordance with Canadian Pat. No. 895,825, air freshener gels can be prepared with gelling agents comprising mixtures of specific carrageenan fractions, namely kappa and iota carrageenan. Specifically, the Canadian Patent teaches the use of a gelling agent composition in air freshener gels comprising kappa and iota fractions of carrageenan in which the weight ratio of the respective components is between about 1.5:1 and about 7:1. The Canadian Patent also teaches the optional addition of calcium and/or potassium ions in the form of their chlorides to the gelling agent composition. The optional addition of calcium or potassium ions to the gelling agent, in accordance with the Canadian Patent, is particularly useful when the gelling agent contains high concentrations of kappa carrageenan.

The air freshener gels obtained in accordance with U.S. Pat. No. 2,927,055 and Canadian Pat. No. 895,825, have been found to exhibit undesirable gel syneresis, i.e., separation of the aqueous medium from the gel caused by gel contraction and/or inadequate water gel strength.

It has now been found that gel syneresis problems associated with the gelling agent combinations set forth in U.S. Pat. No. 2,927,055 and Canadian Pat. No. 895,825, have been overcome by the improved gelling agent composition of the present invention. It was unexpectedly found that the three component gelling agent composition of the present invention, when used to prepare air fresheners gels, yields an air freshener gel exhibiting negligible syneresis and improved water gel strength.

BRIEF SUMMARY OF THE INVENTION

In accordance with the present invention, there is provided an improved air freshener gel consisting essentially of about 1.5 to about 4% of a novel gelling agent, and 98.5 to 96% of an aqueous medium containing a volatile air freshener component. The novel gelling agent comprises: a carrageenan containing at least 40% by weight of the carrageenan, kappa carrageenan, in the range of from about 0.6 to about 2.0%, locust bean gum in the range of from about 0.2 to about 1.0%; and a water soluble ammonium salt having a pH greater than about 5.0 in the range of from about 0.05 to about 1.0% wherein the percent is percent by weight of the air freshener gel. Throughout the specification and examples, all parts and percentages are by weight of the total air freshener gel, unless otherwise noted.

The novel gelling agent of the present invention is useful in the preparation of air freshener gels exhibiting negligible syneresis and improved water gel strength.

DETAILED DESCRIPTION OF THE INVENTION

In accordance with the present invention, there is provided a novel gelling agent comprising carrageenan, locust bean gum, and a water soluble ammonium salt having a pH greater than about 5.0. The term "carrageenan" is used herein to denote a sulfated polysaccharide containing at least 40%, by weight of the carrageenan, kappa carrageenan, and the remainder substantially lambda carrageenan. The carrageenan of the present invention can be derived from a class of seaweed known as Rhodophyceae (red algae), subclass Florideae, and order Gigartinales. Specifically, the carrageenan can be derived from species within the families Gigartinaceae, Solieriaceae, and Hypneaceae, Furcellariaceae and combinations thereof. More specifically, the carrageenan can be derived from the genera Gigartina, Chondrus, Eucheuma, Hypnea, Furcellaria, and combinations thereof. Most specifically, the carrageenan of the present invention can be derived from extracts of *Gigartina stellata, Chondrus crispus, Chondrus ocellatus, Eucheuma cottonii, Hypnea musciformis, Furcellaria fastigiata*, and combinations thereof. Ideally, the carrageenan of the present invention is obtained from *Chondrus crispus* (Irish moss), *Furcellaria fastigiata*, and *Hypnea musciformis*.

The sulfated polysaccharides of the present invention are well known to the prior art and are more fully discussed in the following publications:

"Polysaccharide Gels" by Reese, D.A., Chemistry and Industry, Vol. 19, p. 630 (1972).

Lerring, T., Hoppe, H. A., Schmid, O. J., Marine Algae, p. 342, Cram, DeGruyter & Co. (1969).

The carrageenan of the present invention can be recovered from dried seaweed by first washing the dried seaweed with water, extracting the washed seaweed at an alkaline pH, removing the residue by filtration, drying the extract, and milling the dried carrageenan extract. Any commercially available carrageenan containing at least 40%, by weight of the carrageenan, kappa carrageenan, obtained from the genera and species previously mentioned can be used in the gelling agent of the present invention.

The locust bean gum of the present invention is readily available and generally contains about 88% of D-galacto-D-mannoglycan, 4% pentan, 6% protein, 1% cellulose and 1% ash. Locust bean gum is also known by other names, such as carob gum, gum gatto, gum hevo, jandagum, lakee gum, Rubigum, Lupogum, Luposol, gum Tragon, Tragarab, and Tragasol. Locust bean gum is chemically characterized as a neutral polysaccharide containing substantially D-galacto-D-mannoglycan.

By water soluble ammonium salt having a pH greater than about 5.0 it is meant to denote ammonium salts such as ammonium sulfate, ammonium acetate, ammonium phosphate (dibasic), ammonium chloride, mixtures thereof, or the like. Preferably, the ammonium salt of the present invention is selected from the group consisting of ammonium sulfate, ammonium acetate, ammonium phosphate (dibasic), ammonium chloride, or mixtures thereof. Most preferably, the ammonium salt of the present invention is ammonium chloride.

The ammonium chloride is generally added to the gelling agent composition in dried form. Any commercially available ammonium chloride, i.e., technical or reagent grades, can be used in the novel gelling composition of the present invention.

In accordance with the present invention, the novel gelling agent comprises carrageenan containing at least 40%, by weight of the carrageenan, kappa carrageenan, in the range of from about 0.6 to about 2.0%; locust bean gum in the range of from about 0.2 to about 1.0%; and a water soluble ammonium salt having a pH greater than about 5.0 in the range of from about 0.05 to about 1.0%. Preferably, the gelling agent of the present invention comprises carrageenan containing at least 40%, by weight of the carrageenan, kappa carrageenan, in the range of from about 1.0 to about 1.8%; Locust bean gum in the range of from 0.4 to about 0.8%; and a water soluble ammonium salt having a pH greater than about 5.0 in the range of from about 0.05 to about 1.0%. Most preferably, , the gelling agent of the present invention comprises about 1.5% carrageenan containing at least 40%, by weight of the carrageenan, kappa carrageenan, about 0.6% locust bean gum; and about 0.75% ammonium chloride.

The above described ranges indicated for the components of the novel gelling agent of the present invention have been found necessary to provide air freshener gels exhibiting negligible syneresis, improved water viscosity, and water gel strength. However, the respective ranges of components in the gelling agent composition can be varied within the ranges indicated above to provide air freshener gels exhibiting various degrees of water viscosity, water gel strength, and syneresis, which may be desirable for particular applications.

In formulating air freshener gels, the novel gelling agent of the present invention, typically comprises from about 1.5 to about 4% of the total air freshener gel while the aqueous medium containing an air treating component comprises the remaining 98.5 to 96%. The air treating components comprise about 2 to about 10% of the aqueous medium.

By "air treating component" is meant perfumes, bactericides, essential oils, fungicides, or other desirable air treating components, or mixtures thereof. Preferably, the air treating component is a volatile material at room temperature, compatible with other components in the air freshener gel, and dispersible in aqueous medium. Oils useful for overcoming malodors can be used, such as oil of rose, oil of lime, oil of pine, oil of lemon, oil of spearmint, oil of wintergreen, oil of cedar wood, oil of fir Canadian, and the like. The oils mentioned above may also be used in combination with fragrances such as aromatic esters, aldehydes, ketones, and other compounds known to those skilled in the art of blending fragrances.

In addition, the aqueous medium of the air freshener gel can contain carrier agents which provide increased solubility for the particular oils and fragrances used in the aqueous medium of the air treating gel. The carrier agents can be present in the aqueous medium of the air freshener gel in the range of about 2 to about 6%. Typically, the carrier agents comprise ethanol, isopropanol, ethylene glycol, propylene glycol, hexylene glycol, cellosolve, or the like.

Also, the aqueous medium of the air freshener gel can contain bactericides or fungicides to inhibit microbial or fungal growth within the air freshener gel. The bactericides or fungicides can be present in the aqueous medium of the air freshener gel at about 0.001 to about 0.01%. Typically, the bactericide or fungicide includes sodium benzoate, methyl butyl, or propylparahydroxy benzoate, mixtures thereof, and the like.

Also, the aqueous medium of the air freshener gel can contain water soluble or oil soluble dyes which impart color to the air freshener gel. Particularly, the water soluble or oil soluble dyes can be present in the aqueous medium of the air freshener gel up to about 0.05%. Typical examples of suitable water soluble or oil soluble dyes are Rose Bengal dye, Uramine dye, Rhodamine dye, and the like.

In addition, the aqueous medium of the air freshener gel can contain emulsifiers well known in the art. The emulsifiers may be anionic, such as the alkyl sulfonates, alkyl sulfates, or alkyl ether sulfates, or may be nonionic compounds such as the polyethoxylate ethers, sorbitan esters, or polyethoxylates of sorbitan esters.

The air freshener gels of the present invention are typically prepared as follows: dry blending the gelling agent components, i.e., carrageenan, locust bean gum, and ammonium chloride; dispersing the dry blended gelling agent components in water having a temperature above about 90° F. with stirring; heating the dispersed gelling agent to a temperature between about 150° F. and about 190° F. with stirring until the dispersed gelling agent is completely dissolved; cooling the aqueous solution of gelling agent to a temperature between about 135° F. and about 150° F; adding an air treating agent to the cool solution of gelling agent while stirring to provide a uniform mixture of air freshener components; and cooling to a temperature below about 100° F. to cause gel formation and provide the air freshener gel. Preferably, the dispersed gelling agent is heated to a temperature of about 180° F. with stirring until the solids are completely dissolved. Also, it is preferred that the uniform mixture of air freshener gel be poured into a suitable container or mold so as to provide a gel having the desired shape.

The novel gelling agent of the present invention is further illustrated by the examples which follow. All parts and percentages are by weight unless otherwise noted.

EXAMPLE 1

The air freshener gel can be prepared with the novel gelling agent composition of the present invention as follows. 500 grams of air freshener gel were prepared by first dry blending 7.5 grams of carrageenan, 3.0 grams of commercial grade locust bean gum, and 3.75 grams of reagent grade ammonium chloride. The carrageenan comprises substantially kappa carrageenan, i.e., 70–80% kappa carrageenan, and 20–30% lambda carrageenan. The carrageenan used in this example was obtained from Stauffer Chemical Company as an extract of *Chondrus crispus* (Irish Moss).

The dry blended gelling agent was thereafter dispersed in about 440 grams of water by stirring. The dispersed gelling agent was then heated to a temperature of about 180° F. with stirring until the dispersed solids were dissolved. The gelling agent solution was then allowed to cool to about 150° F. The weight of the gelling agent solution was adjusted to 460 grams by the addition of water. To the gelling agent solution, at a temperature of about 150° F. there was added 40 grams of the air treating agent comprising 6.6 grams of oil of lemon, 3.3 grams of oil of lime, 20 grams of isopropyl alcohol, 10 grams of ethylene glycol, and 0.1 gram of Uramine dye. The air treating agent was then blended to provide a uniform air freshener dispersion. The air freshener dispersion was then poured into crystallizing dishes measuring 7.0 centimeters in diameter by 5.0 centimeters in depth. The air freshener dispersion was then allowed to cool to room temperature to provide an air freshener gel.

Air freshener gel syneresis was determined as follows: the crystallizing dish containing the air freshener gel was covered with paraffin paper and stored in a constant temperature incubator at 40° F. After overnight incubation, the air freshener gel was removed from the incubator and allowed to equilibrate to room temperature. The paraffin paper was then removed from the air freshener gel, and the gel carefully tapered into a preweighed paper towel. The air freshener gel was then rotated on the paper towel to allow the paper towel to absorb excess liquid from the gel. The weight of the air freshener gel and the weight of the paper towel were then determined. The percent syneresis is expressed as the amount of liquid absorbed by the paper towel, divided by the total gel weight, multiplied by 100.

The air freshener gel sample in Example 1 was found to exhibit a syneresis rate of less than 0.3%, determined as described above. Visually, the air freshener gel prepared in accordance with Example 1 exhibited no apparent syneresis. Therefore, air freshener gels exhibiting less than 0.3% syneresis, determined as described above, exhibit negligible syneresis, i.e., no free flowing liquid can be seen.

The water viscosity of the air freshener dispersion was determined as follows. The water viscosity of the air freshener dispersion was determined at 145° F. with a Brookfield viscosimeter, model LVT, using the appropriate spindle and rotation rate. The water viscosity of the air freshener dispersion was 1100 centipoise, determined as described above.

The water gel strength of the air freshener gel was determined in a gel tester, Model GT-3 from Marine Colloids, Inc. The gel tester was used with a flat head plunger measuring 0.431 inches in diameter. A dietetic scale was placed directly beneath the plunger and was used to measure the break force required for the plunger to penetrate the gel material being measured. After the syneresis evaluation, the air freshener gel was placed in a crystallizing dish. The water gel strength was then determined by placing the crystallizing dish containing the air freshener gel sample to be measured on top of the scale. The scale was then zeroed and the flat head plunger brought down onto the surface of the gel material. The plunger was continuously forced into the gel until a maximum force required to break the gel surface was indicated. The weight indicated on the scale required to break the gel surface for the sample of Example 1 was 710 grams.

Th composition of the air freshener gel prepared in accordance with Example 1 is set forth in Table I. The results of the air freshener evaluation relating to water, viscosity, water gel strength, and syneresis are shown in Table VI.

TABLE I

| Air Freshener Gel Composition - Example No. 1 | |
|---|---|
| Ingredients | Percent (by weight of final gel) |
| Gelling Agent | |
| Carrageenan | 1.5 |
| Locust Bean Gum | 0.6 |
| Ammonium Chloride | 0.75 |
| Air Treating Components | |
| Oil of Lemon | 1.33 |
| Oil of Lime | 0.67 |
| Isopropyl Alcohol | 4.0 |
| Ethylene Glycol | 2.0 |
| Uramine Dye | 0.02 |
| Aqueous Medium | |
| Water | 89.13 |

EXAMPLE 2

This example represents a control sample of air freshener gel prepared in accordance with Example I of U.S. Pat. No. 2,927,055. The air freshener gel was prepared in accordance with the process described for Example 1 above. The air freshener gel composition is presented in Table II.

TABLE II

| Air Freshener Gel Composition (Control) | |
|---|---|
| Ingredients | Percent (By weight of Final Gel) |
| Gelling Agent | |
| Carrageenan | 1.5 |
| Locust Bean Gum | 0.25 |
| Potassium Chloride | 0.5 |
| Sodium Carboxymethyl Cellulose | 0.25 |
| Air Treating Components | |
| Oil of Rose | 3.0 |
| Isopropyl Alcohol | 4.0 |
| Ethylene Glycol | 2.0 |
| Water - Soluble Chlorophyl | 0.1 |
| Aqueous Medium | |
| Water | 88.40 |

The water viscosity, water gel strength, and syneresis were determined as previously described in Example 1. The results of the air freshener evaluation relating to water viscosity, water gel strength, and syneresis are shown in Table VI.

EXAMPLE 3

An air freshener gel was prepared in accordance with Example 1 of Canadian Patent No. 895,825. The air freshener gel was prepared by the method set forth above in Example 1. The composition of the air freshener gel is set forth below in Table III.

TABLE III

Air Freshener Gel Composition

| Ingredients | Percent (By Weight of Final Gel) |
|---|---|
| Gelling Agent | |
| Carrageenan | |
| Kappa | 2.33 |
| Iota | 0.67 |
| Air Treating Component | |
| Oil of Lemon | 2.31 |
| Oil of Lime | 1.00 |
| Ethylene Glycol | 4.0 |
| Sodium Chlorophyllin | 0.5 |
| Emulsifier (Tween 20, Atlas Chemical Company) | 1.88 |
| Sodium Benzoate | 0.1 |
| Aqueous Medium | |
| Water | 87.21 |

The air freshener gel prepared in accordance with Example 3 was evaluated with respect to water viscosity, water gel strength and syneresis, in accordance with the methods set forth in Example 1. The results of the air freshener gel evaluation are shown in Table VI.

EXAMPLE 4

An air freshener gel was prepared with the composition set forth in Example 2 of Canadian Patent No. 895,825. The method of preparation of the air freshener gel was as set forth in Example 1 above. The composition of the air freshener gel is set forth below in Table IV.

TABLE IV

Air Freshener Gel Composition

| Ingredients | Percent (By Weight of Final Gel) |
|---|---|
| Gelling Agent | |
| Carrageenan | |
| Kappa | 2.0 |
| Iota | 0.3 |
| Calcium Chloride | 0.75 |
| Air Treating Components | |
| Oil of Rose | 2.0 |
| Ethyl Alcohol | 3.0 |
| Rose Bengal Dye | 0.5 |
| Emulsifier (Tween 20, Atlas Chemical Company) | 1.0 |
| Sodium Benzoate | 0.1 |
| Aqueous Medium | |
| Water | 90.35 |

The air freshener gel prepared as described above was evaluated with respect to water viscosity, water gel strength, and syneresis. The results of this evaluation are set forth in Table VI.

EXAMPLES 5-9

In Examples 5-9, air freshener gels were prepared in accordance with the method set forth in Example 1 above. The gelling agent compositions were varied as set forth below in Table V. The air freshener gels prepared in accordance with Examples 5-9 were evaluated with respect to water viscosity, water gel strength, and syneresis, as previously set forth in Example 1. The results of these evaluations are set forth in Table VI.

EXAMPLES 10 and 11

In Example 10, an air freshener gel was prepared with carrageenan obtained from *Chordrus crispus* containing about 80% by weight of the carrageenan, kappa carrageenan. The air freshener gel composition is set forth in Table V. The method of preparation of air freshener gel for this Example was as set forth in Example 1 above.

In Example 11, an air freshener gel was prepared with a polysaccharide extract from *Hypnea musciformis* corresponding to carrageenan. The composition of the air freshener gel prepared with this particular gelling agent combination is set forth in Table V. The method of preparation of air freshener gel in this example was as set forth above in Example 1.

Examples 10 and 11 were evaluated with respect to water viscosity, water gel strength, and syneresis as set forth above in Example 1. The results of these evaluations are set forth in Table VI.

TABLE V

| Example No. | Gelling Agent | | | Air Treating Components | | | Aqueous | |
|---|---|---|---|---|---|---|---|---|
| | Carrageenan | Locust Bean Gum | Ammonium Chloride | Essential Oil | Isorpopyl Alcohol | Ethylene Glycol | Coloring | Medium Water |
| 5 | 1.0 | 1.0 | 1.0 | 2.0[1] | 4.0 | 2.0 | 0.02[2] | 88.98 |
| 6 | 2.0 | 0.2 | 0.3 | " | " | " | " | 89.48 |
| 7 | 1.5 | 0.75 | 0.73 | " | " | " | " | 88.98 |
| 8 | 0.6 | 0.6 | 0.6 | " | " | " | " | 90.58 |
| 9 | 2.0 | 0.6 | 0.1 | " | " | " | " | 89.28 |
| 10 | 1.35 | 0.6 | 0.75 | " | " | " | " | 89.28 |
| 11 | 1.35[3] | 0.6 | 0.75 | " | " | " | " | 89.28 |

[1]Oil of Rose
[2]Rose Bengal Dye
[3]Carrageenan from *Hypnea musciformis*

TABLE VI

Air Freshener Gel Evaluation

| Example | Water Viscosity (Centipoise) | Water Gel Strength (grams) | Syneresis (Percent) |
|---|---|---|---|
| 1 | 1100 | 710 | 0.20 |
| 2 | 260 | 690 | 0.67 |
| 3 | 477 | 88 | 0.27 |
| 4 | 105 | 87 | 0.44 |
| 5 | 2632 | 705 | 0.17 |
| 6 | 214 | 463 | 0.21 |
| 7 | 2064 | 697 | 0.21 |
| 8 | 390 | 517 | 0.34 |
| 9 | 2308 | 690 | 0.34 |
| 10 | 728 | 727 | 0.16 |
| 11 | 347 | 727 | 0.26 |

It is apparent from Table VI with respect to Examples 1-4, that the air freshener gel prepared with the novel gelling agent composition of the present invention exhibits improved physical properties in that the level of syneresis is below 0.5%, the water gel strength is above 400 grams, and the water viscosity is below 2700 centipoise. In contrast, it is apparent from Table VI, Example 2, that air freshener gels prepared in accordance with U.S. Pat. No. 2,927,055 wherein gelling agents are used comprising carrageenan, locust bean gum, potassium chloride, and carboxymethylcellulose exhibit an undesirable level of gel syneresis, i.e., 0.67%. Also, it is apparent from Table VI, Example 3, which represents an air freshener gel prepared in accordance with Example 1 of Canadian Pat. No. 895,825, wherein an air freshener gel is prepared with a gelling agent comprising kappa carrageenan and iota carrageenan that the water gel strength of the air freshener gel is undesirable, i.e., 88 grams. With respect to water gel strength, it has been found that air freshener gels exhibiting water gel strengths less than about 400 grams are undesirable because the gel is incapable of retaining its original shape. Furthermore, it is apparent from Table VI, Example 4, which represents an air freshener gel prepared in accordance with Example 2 of Canadian Pat. No. 895,825, wherein a gelling agent comprising kappa carrageenan, iota carrageenan, and calcium chloride is used that the air freshener gel exhibits undesirable water gel strength, i.e., 87.

It is apparent from Table VI, Examples 5-9 that air freshener gels can be prepared with the novel gelling agent composition of the present invention, i.e., carrageenan, locust bean gum, and ammonium chloride. The level of syneresis, water gel strength, and water viscosity as set forth in Table VI, are well within the desirable limits required for these evaluation parameters.

It is apparent from Table VI, Examples 10 and 11 that air freshener gels exhibiting desirable water viscosity, water gel strength, and syneresis properties can be prepared with gelling agents containing substantially kappa carrageenan, as indicated by Examples 10, and a polysaccharide extract from *Hypnea musciformis*.

Variations may be made in proportions, procedures, and materials without departing from the scope of this invention as defined in the following claims.

What is claimed is:

1. In an air freshener gel consisting essentially of about 1.5 to 4% of a gelling agent, and about 98.5 to 96% of an aqueous medium containing a volatile air freshener component; the improvement which comprises a gelling agent comprising:
   a. from about 0.6 to about 2% of a carrageenan of which at least 40% by weight is the kappa fraction,
   b. from about 0.2 to about 1.0% of locust bean gum; and
   c. from about 0.05 to about 1.0% of a water soluble ammonium salt having a pH greater than about 5.0 selected from the group consisting of ammonium chloride, ammonium sulfate, ammonium acetate, ammonium phosphate (dibasic) and mixtures thereof, wherein said percent is percent by weight of said air freshener gel.

2. The gelling agent of claim 1 wherein said carrageenan containing at least 40% by weight of the kappa fraction is obtained from extracts and combinations of extracts from seaweed of the class Rhodophyceae, subclass Florideae, order Gigartinales, and family selected from the group consisting of Gigartinaceae, Solieriaceae, Hypneaceae, Furcellariaceae and combinations of said seaweed.

3. The gelling agent of claim 1 wherein said carrageenan containing at least 40% by weight of the kappa fraction is obtained from extracts and combinations of extracts from seaweed of the class Rhodophyceae of the genera selected from the group consisting of Gigartina, Chondrus, Eucheuma, Hypnea, Furcellaria, and combinations of said seaweed.

4. The gelling agent of claim 1 wherein said carrageenan containing at least 40% by weight of the kappa fraction is obtained from extracts and combinations of extracts from seaweed of the class Rhodophyceae of the species selected from the group consisting of *Gigartina stellata, Chondrus crispus, Chondrus ocellatus, Eucheuma cottonii, Hypnea musciformis, Furcellaria fastigiata* and combinations of said seaweed.

5. The gelling agent of claim 4 wherein said specie is *Chondrus crispus*.

6. The gelling agent of claim 4 wherein said specie is *Furcellaria fastigiata*.

7. The gelling agent of claim 4 wherein said specie is *Hypnea musciformis*.

8. The air freshener gel of claim 1 wherein said gelling agent comprises:
   a. from about 1.0 to about 1.8% of said carrageenan containing at least 40% by weight of the kappa fraction,
   b. from about 0.4 to about 0.8% of said locust bean gum; and
   c. from about 0.5 to about 1.0% of said water soluble ammonium salt having a pH greater than about 5.0.

9. The air freshener gel of claim 8 wherein said gelling agent comprises:
   a. about 1.5% of said carrageenan containing at least 40% by weight of the kappa fraction,
   b. about 0.6% of said locust beam gum; and
   c. about 0.75% of ammonium chloride.

10. In an air freshener gel consisting of about 2.5 to 3.0% of a gelling agent and about 97.5 to 97% of an aqueous medium containing a volatile air freshener component; the improvement which comprises a gelling agent comprising:
    from about 1.0 to about 1.8% of a carrageenan containing at least 40% by weight of the kappa fraction,
    b. from about 0.4 to about 0.8% of locust bean gum; and
    c. from about 0.5 to about 1.0% of a water soluble ammonium salt selected from the group consisting of ammonium chloride, ammonium sulfate, ammonium acetate, ammonium phosphate (dibasic), and mixtures thereof, wherein said percent is percent by weight of said freshener gel.

11. The gelling agent of claim 10 wherein said carrageenan containing at least 40% by weight of the kappa fraction is obtained from extracts and combinations of extracts from seaweed of the class Rhodophyceae of the genera selected from the group consisting of Gigartina, Chondrus, Eucheuma, Hypnea, Furcellaria, and combinations of said seaweed.

12. The gelling agent of claim 10 wherein said carrageenan containing at least 40% by weight of the kappa fraction is obtained from extracts and combinations of extracts from seaweed of the class Rhodophyceae of the species selected from the group consisting of *Gigartina stellata, Chondrus crispus, Chondrus oscellatus, Eucheuma cottonii, Hypnea musciformis, Furcellaria fastigiata*, and combinations of said seaweed.

13. The gelling agent of claim 12 wherein said specie is Furcellaria fastigiata.

14. The gelling agent of claim 12 wherein said specie is Hypnea musciformis.

15. The gelling agent of claim 12 wherein said specie is Choadrus crispus.

16. The air freshener gel of claim 10 wherein said gelling agent comprises:
    a. about 1.5% of said carrageenan containing at least 40% by weight of the kappa fraction,
    b. about 0.6% of said locust bean gum; and
    c. about 0.75% of ammonium chloride.

* * * * *